US008257248B2

(12) United States Patent
Yoshizawa et al.

(10) Patent No.: US 8,257,248 B2
(45) Date of Patent: Sep. 4, 2012

(54) BODY-INSERTABLE APPARATUS AND BODY-INSERTABLE APPARATUS SYSTEM

(75) Inventors: Fukashi Yoshizawa, Tokyo (JP); Youhei Sakai, Tokyo (JP); Seiichiro Kimoto, Tokyo (JP)

(73) Assignee: Olympus Corporation, Tokyo (JP)

( * ) Notice: Subject to any disclaimer, the term of this patent is extended or adjusted under 35 U.S.C. 154(b) by 1420 days.

(21) Appl. No.: 11/793,348

(22) PCT Filed: Mar. 9, 2005

(86) PCT No.: PCT/JP2005/004114
§ 371 (c)(1),
(2), (4) Date: Jun. 18, 2007

(87) PCT Pub. No.: WO2006/095420
PCT Pub. Date: Sep. 14, 2006

(65) Prior Publication Data
US 2008/0076965 A1 Mar. 27, 2008

(51) Int. Cl.
*A61B 1/00* (2006.01)
*A61B 1/04* (2006.01)
(52) U.S. Cl. .................... 600/118; 600/103; 348/76
(58) Field of Classification Search .............. 510/162, 510/495, 175, 461; 600/118, 109, 103; 348/74, 348/76
See application file for complete search history.

(56) References Cited

U.S. PATENT DOCUMENTS

| | | | | |
|---|---|---|---|---|
| 3,670,722 A | * | 6/1972 | Kosaka | 600/109 |
| 4,310,228 A | * | 1/1982 | Terada | 396/17 |
| 6,428,469 B1 | * | 8/2002 | Iddan et al. | 600/109 |
| 6,517,478 B2 | * | 2/2003 | Khadem | 600/117 |
| 6,635,011 B1 | * | 10/2003 | Ozawa et al. | 600/178 |
| 6,833,912 B2 | * | 12/2004 | Lei et al. | 356/124 |
| 7,001,329 B2 | * | 2/2006 | Kobayashi et al. | 600/114 |
| 7,195,588 B2 | * | 3/2007 | Homan et al. | 600/118 |
| 7,419,468 B2 | * | 9/2008 | Shimizu et al. | 600/117 |

(Continued)

FOREIGN PATENT DOCUMENTS

EP 1 510 169 A1 3/2005
(Continued)

OTHER PUBLICATIONS

Supplementary European Search Report dated Feb. 11, 2010.
(Continued)

*Primary Examiner* — Philip R Smith
*Assistant Examiner* — William Chou
(74) *Attorney, Agent, or Firm* — Scully, Scott, Murphy & Presser, P.C.

(57) ABSTRACT

A body-insertable apparatus that is used in a state of being introduced in a body of a subject, and that performs a predetermined function inside the body of the subject includes an imaging circuit 27, a battery 40 that supplies with energy to be used to drive the imaging circuit 27, a power switch 33 that switches energy supply to the imaging circuit 27 from the battery 40, a switch control circuit 32 that performs a switching control of the power switch 33, and a signal detecting circuit 31 that detects a magnet and that transmits, to the switch control circuit, a control signal to cause the power switch 33 to toggle the switching control based on this detection state, and is possible to be turned on and off a main switch at a desirable timing before introduction into the body of the subject, thereby achieving energy saving in which a life of a battery is saved, and suppressing unnecessary radio wave radiation.

13 Claims, 16 Drawing Sheets

U.S. PATENT DOCUMENTS

| | | | |
|---|---|---|---|
| 7,452,328 B2* | 11/2008 | Homan et al. | 600/180 |
| 7,922,653 B2* | 4/2011 | Homan | 600/118 |
| 2001/0035902 A1 | 11/2001 | Iddan et al. | |
| 2001/0051762 A1* | 12/2001 | Murata et al. | 600/118 |
| 2003/0093503 A1* | 5/2003 | Yamaki et al. | 709/220 |
| 2003/0181788 A1 | 9/2003 | Yokoi et al. | |
| 2003/0229268 A1 | 12/2003 | Uchiyama et al. | |
| 2004/0087832 A1* | 5/2004 | Glukhovsky et al. | 600/118 |
| 2004/0138552 A1* | 7/2004 | Harel et al. | 600/407 |
| 2004/0193010 A1* | 9/2004 | Fujimori et al. | 600/118 |
| 2004/0236181 A1* | 11/2004 | Honda et al. | 600/118 |
| 2004/0236182 A1* | 11/2004 | Iddan et al. | 600/118 |
| 2004/0254455 A1* | 12/2004 | Iddan | 600/424 |
| 2005/0043634 A1* | 2/2005 | Yokoi et al. | 600/476 |
| 2005/0049461 A1* | 3/2005 | Honda et al. | 600/160 |
| 2005/0054897 A1* | 3/2005 | Hashimoto et al. | 600/118 |
| 2005/0065407 A1* | 3/2005 | Nakamura et al. | 600/160 |
| 2005/0272973 A1* | 12/2005 | Kawano et al. | 600/102 |
| 2006/0155174 A1* | 7/2006 | Glukhovsky et al. | 600/301 |
| 2006/0241578 A1* | 10/2006 | Honda | 606/32 |
| 2007/0073106 A1* | 3/2007 | Uchiyama | 600/118 |
| 2007/0173691 A1* | 7/2007 | Yokoi et al. | 600/118 |
| 2007/0185382 A1* | 8/2007 | Shimizu et al. | 600/118 |
| 2007/0225560 A1* | 9/2007 | Avni et al. | 600/118 |
| 2007/0270641 A1* | 11/2007 | Kimoto et al. | 600/109 |
| 2008/0033243 A1* | 2/2008 | Meron et al. | 600/109 |
| 2008/0033257 A1* | 2/2008 | Yokoi et al. | 600/300 |
| 2008/0045792 A1* | 2/2008 | Shimizu et al. | 600/118 |
| 2008/0103363 A1* | 5/2008 | Levy et al. | 600/160 |
| 2008/0106596 A1* | 5/2008 | Iddan et al. | 348/76 |
| 2008/0183041 A1* | 7/2008 | Fujimori et al. | 600/118 |
| 2008/0188712 A1* | 8/2008 | Shimizu et al. | 600/118 |
| 2010/0091100 A1* | 4/2010 | Sarwari | 348/76 |

FOREIGN PATENT DOCUMENTS

| | | |
|---|---|---|
| EP | 1 598 000 A1 | 11/2005 |
| JP | 2004-261240 | 9/2004 |
| JP | 2005-21651 | 1/2005 |
| JP | 2005-81005 | 3/2005 |
| WO | WO 01/35813 | 5/2001 |
| WO | 2004/075739 | 9/2004 |

OTHER PUBLICATIONS

European Official Action dated Apr. 27, 2010.
English language abstract of JP 2004-261240.
Extended European Search Report dated Aug. 22, 2011 in counterpart European Patent Application No. EP 11004122.5.

* cited by examiner

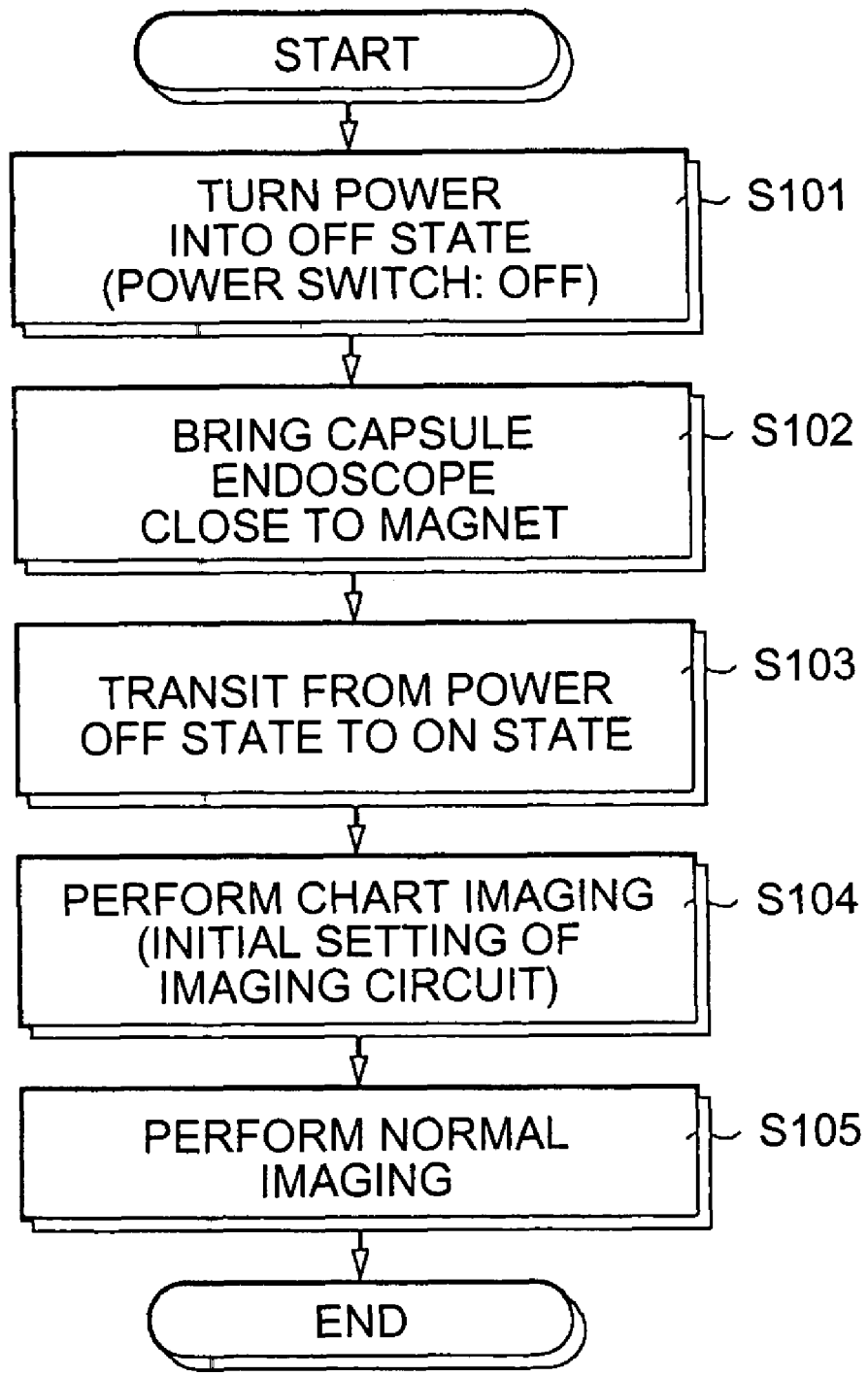

BODY-INSERTABLE APPARATUS AND BODY-INSERTABLE APPARATUS SYSTEM

TECHNICAL FIELD

The present invention relates to a body-insertable apparatus that is used in a state of being introduced inside a body of a subject and that performs predetermined functions inside the subject, and a body-insertable apparatus system.

BACKGROUND ART

Recently, in the field of endoscope, a swallowable capsule endoscope has appeared. The capsule endoscope is provided with an imaging function and a radio communication function. The capsule endoscope has a function of sequentially picking up images after the capsule endoscope is orally swallowed by a patient for observation (examination) until naturally discharged out of a human body, while passing through body cavities, for example, inside organs such as stomach and small intestine, according to the peristalsis thereof.

Image data obtained inside the body by the capsule endoscope while moving inside the body cavities is sequentially transmitted to the outside by radio communication, and stored in a memory provided in an external receiver. If the patient carries the receiver having such radio communication function and memory function, the patient can freely move even during the period from swallow of the capsule endoscope until discharge thereof. Thereafter, doctors and nurses can perform diagnosis based on the image data stored in the memory by displaying an image of the organs on a display.

Most capsule endoscopes take such a configuration that a driving power is provided by an embedded power supply. Further, some propose a configuration of the capsule endoscope including a lead switch which is provided in the capsule endoscope and turned on and off in response to an external magnetic field and a permanent magnet which is provided in a package covering the capsule endoscope and provides the magnetic field to control the driving of the capsule endoscope. The lead switch provided in the capsule endoscope has a configuration so that the lead switch maintains an off state under an environment in which the external magnetic field having intensity higher than predetermined intensity is applied, and is turned on when the intensity of the external magnetic field is lowered. Therefore, the capsule endoscope is not driven in a state of being packed in the package, and starts being driven when the capsule endoscope is taken out from the package to be released from the influence of the permanent magnet. With such a configuration, it is possible to prevent the driving of the capsule endoscope while the capsule endoscope is packed in the package (for example, see Patent Document 1).

Patent Document 1: International Publication No. WO01/35813 pamphlet

DISCLOSURE OF INVENTION

Problem to be Solved by the Invention

If a mechanism to control the driven state of the capsule endoscope as described above is provided, however, since the capsule endoscope turns into a state, in which the capsule endoscope can start driving, upon being removed from the package, the a power source such as a battery is consumed if the capsule endoscope is left for a long time after taken out of the package.

In addition, sometimes it is desirable that the capsule endoscope be checked for shipment after the capsule endoscope is packed in the package, however, since the conventional capsule endoscope cannot be brought into a driving state while being packed in the package, it is difficult to perform the inspection flexibly for commercial distribution while maintaining the capsule endoscope in an energy-saving state.

An initial setting for imaging including various corrections such as white balance correction, adjustment, and a default setting are required before the capsule endoscope is brought into use after taken out from the package. Since the initial setting consumes large electricity for driving an imaging circuit, it is preferable to complete the initial setting in a short time.

The present invention has been achieved in view of the above, and it is an object of the present invention to provide a body-insertable apparatus and a body-insertable apparatus system in which a main power can be turned on and off at a desirable timing, and inadvertent power consumption is suppressed to save power consumption.

Means for Solving Problem

A body-insertable apparatus according to one aspect of the present invention is used in a state of being introduced inside a body of a subject and performs a predetermined function inside the body of the subject, and includes a function executing unit that performs the predetermined function; an energy supply source that supplies with energy to be used to drive the function executing unit; an external-signal detecting unit that detects an external control signal input from outside, and that generates a control signal based on a detection state of the external control signal; a switch that controls supply of the energy to the function executing unit from the energy supply source; an energy supply control unit that causes the switch to toggle in accordance with the control signal from the external-signal control detecting unit.

Moreover, in the body-insertable apparatus, the energy supply control unit may include a ½ frequency divider circuit that frequency-divides the control signal output from the external-signal detecting unit by two, and that causes the switch to toggle according to the control signal that has been frequency-divided by two.

Furthermore, in the body-insertable apparatus, the energy supply control unit may include a state maintaining unit that maintains the detection state of the external control signal detected by the external-signal detecting unit.

Moreover, in the body-insertable apparatus, the state maintaining unit may include a second switch that performs a switching operation according to detection of the external control signal by the external-signal detecting unit; and a control circuit that controls to eliminate direct current flowing through the second switch, in response to the switching operation between an on state and an off state performed by the second switch.

Furthermore, in the body-insertable apparatus, the state maintaining unit may include an output control circuit that generates a reverse signal obtained by reversing the control signal output from between the external-signal detecting unit and a ground, and that outputs a re-reverse signal obtained by further reversing the reverse signal to the switch; a first control circuit including a capacitor that is arranged between the energy supply source and the external-signal detecting unit, and a first switch that is connected to the capacitor in parallel and that is turned on and off based on the re-reverse signal indicating on or off; and a second control circuit including a resistor that is arranged between an output end of the control signal and a ground, and a second switch connected in series on a side of the ground and that turned on and off based on the reverse signal indicating on or off.

Moreover, the body-insertable apparatus may further include a ½ frequency divider circuit that frequency-divides the re-reverse signal output from the output control circuit by two, and that causes the switch to toggle according to the control signal that has been frequency-divided by two, the ½ frequency divider circuit arranged between the output control circuit and the switch.

Furthermore, the body-insertable apparatus may further include a different external-signal detecting unit that detects a different external signal of which a detection mode is different, and that transmits a control signal to cause the switch to toggle to the energy supply control unit according to a detection state; and a logical sum circuit that calculates a logical sum of the control signal output from the external-signal detecting unit and the control signal output from the different external signal detecting unit and outputs the logical sum to the switch.

Moreover, in the body-insertable apparatus, as the function executing unit, an imaging unit may be further included, an object for an initial setting may be provided, externally to the body-insertable apparatus, in advance within an imaging area of the imaging unit, and the imaging unit may include a control unit that performs the initial setting at a time of initial energy supply.

Furthermore, in the body-insertable apparatus, at least one of the ½ frequency divider circuit and the output control circuit may include a CMOS circuit.

Moreover, in the body-insertable apparatus, at least one of the switch, the first switch, and the second switch may include a MOS transistor.

Furthermore, in the body-insertable apparatus, the external-signal detecting unit may be a lead switch that detects a magnetic force as the external control signal.

Moreover, in the body-insertable apparatus, the different external-signal detecting unit may be a radio receiving unit that receives a radio signal.

Furthermore, a body-insertable apparatus system according to another aspect of the present invention includes an external-signal generating device that generates a successive pulse signal as an external control signal; and a body-insertable apparatus that includes a function executing unit that performs a predetermined function inside a body of a subject; an energy supply source that supplies with energy to be used to drive the function executing unit; an external-signal detecting unit that detects the external control signal input from outside; a measuring unit that measures a number of pulses in the successive pulse signal based on a result of detection by the external-signal detecting unit, and that outputs a control signal on detecting a predetermined number of pulses successively; a switch that controls supply of the energy to the function executing unit from the energy supply source; and an energy supply control unit that causes the switch to toggle according to the control signal from the measuring unit, the body-insertable apparatus being used in a state of being introduced inside the body of the subject.

Moreover, in the body-insertable apparatus system, the external-signal generating device may further include a position detecting unit that detects approach of the body-insertable apparatus, and the external-signal generating device may generate the successive pulse signal when the approach of the body-insertable apparatus is detected.

Effect of the Invention

In a body-insertable apparatus according to the present invention, since the energy supply from the energy supply source to the function executing unit is turned on and off in response to the toggle operation based on an external control signal, the energy supply from the energy supply source can be turned on and off at desirable timing even if the body-insertable apparatus is still in the package, as far as the body-insertable apparatus has not been introduced into the subject, whereby unnecessary power consumption of the energy supply source and unnecessary radio wave radiation can be suppressed.

BRIEF DESCRIPTION OF DRAWINGS

FIG. 16 is a flowchart showing procedures of an initial setting of the capsule endoscope shown in FIG. 15.

EXPLANATIONS OF LETTERS OR NUMERALS

Figure 1:
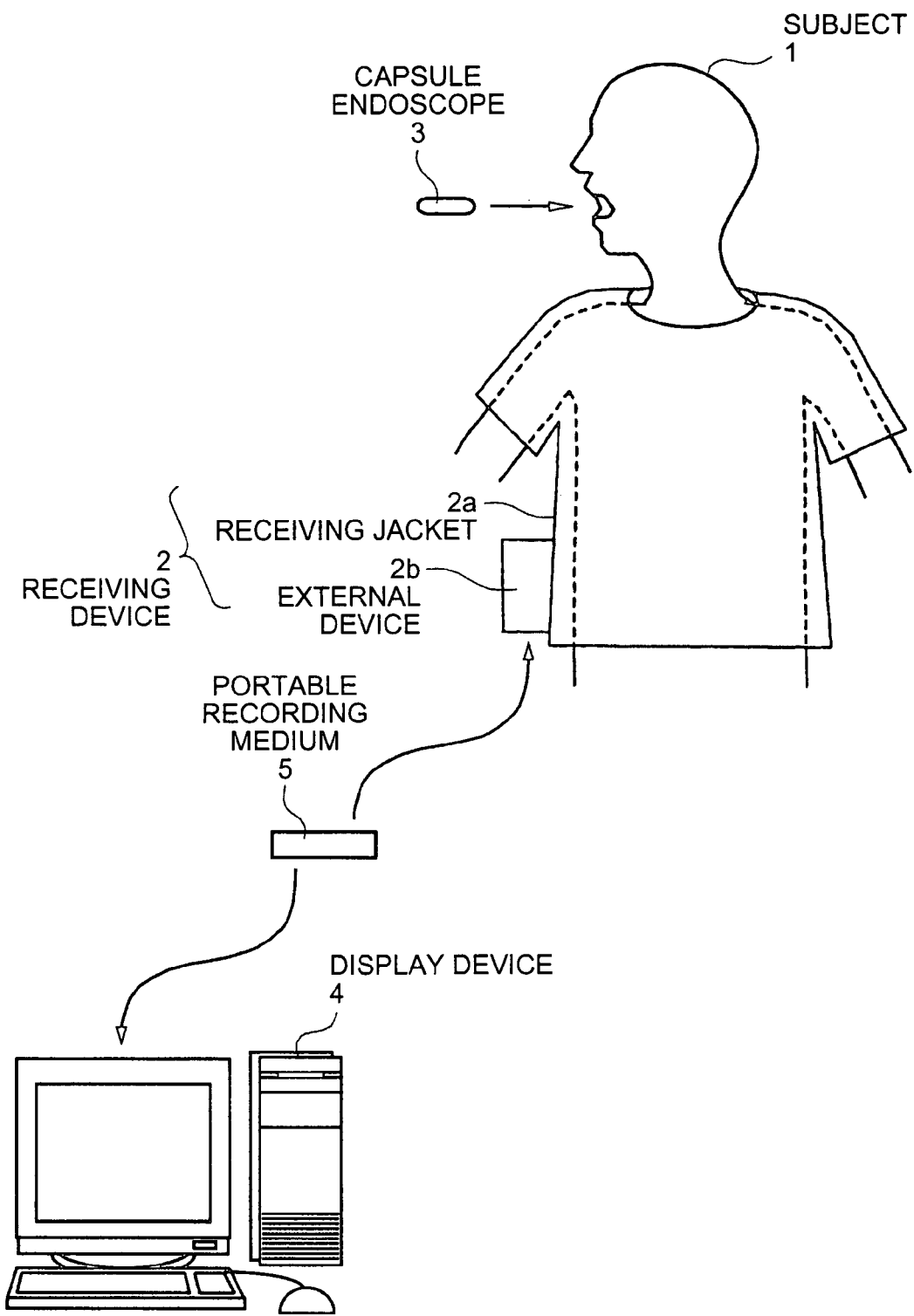
FIG. 1 is a schematic diagram showing an overall configuration of a radio intra-subject information acquiring system that includes a body-insertable apparatus according to a first embodiment of the present invention.

1 Subject
2 Receiving device
2a Receiving jacket
2b External device
3 Capsule endoscope
4 Display device
5 Portable recording medium
11 RF receiving unit 12 Image processing unit
13 Storage unit
18 Power supply unit
19 LED
20 LED driving circuit
21 CCD
22 Signal processing circuit
23 RF transmitting unit
24 Transmitting antenna unit
25 CCD driving circuit
26 System control circuit
27 Imaging circuit
30, 130, 230, 330, 530 Power switch circuit
31 Signal detecting circuit
32 Switch control circuit
33, 133, M3 Power switch
34 Driving controller
35 Sensor unit
40 Battery
50 Magnet
101 Main circuit
130 Power switch circuit
132 ½ frequency divider circuit
400 OR circuit
401 Antenna
402 Receiving circuit
500 External-signal generating device
501 Driving power source
531 Counter
550 Electromagnet
600 Position detecting circuit
601 Switch
A1 to An Receiving antenna
CT1 First control circuit
CT2 Second control circuit
CT3 Third control circuit
S1 Lead switch
M1 n-channel MOS transistor
M2 p-channel MOS transistor

BEST MODE(S) FOR CARRYING OUT THE INVENTION

Exemplary embodiments of a body-insertable apparatus and a body-insertable apparatus system according to the present invention will be explained below.

First Embodiment

First, a radio intra-subject information acquiring system that includes a body-insertable apparatus according to a first embodiment will be explained. A capsule endoscope will be explained as an example of the body-insertable apparatus in the following description of the radio intra-subject information acquiring system according to the first embodiment.

FIG. 1 is a schematic diagram showing an overall configuration of the radio intra-subject information acquiring system according to the first embodiment. As shown in FIG. 1, the radio intra-subject information acquiring system includes a receiving device 2 that has a radio receiving function and a capsule endoscope 3 that is introduced inside a body of a subject 1, that operates by means of a driving power controlled by a radio signal transmitted from the receiving device 2, and that acquires images inside body cavities to transmit data to the receiving device 2. Moreover, the radio intra-subject information acquiring system includes a display device 4 that displays the images of the body cavities based on the data received by the receiving device 2, and a portable recording medium 5 that delivers data between the receiving device 2 and the display device 4. The receiving device 2 includes a receiving jacket 2a worn by the subject 1 and an external device 2b that performs processing on the radio signal transmitted through the receiving jacket 2a.

The display device 4 displays the body-cavity images acquired by the capsule endoscope 3, and has a configuration similar to a workstation and the like to perform image display based on the data obtained by the portable recording medium 5. Specifically, the display device 4 can take a configuration to directly display the images with a CRT display, a liquid crystal display, and the like, or can take a configuration to output the images to other medium, as in a printer.

The portable recording medium 5 is configured to be attachable/detachable to/from the external device 2b and the display device 4, and output and recording of information are allowed when the portable recording medium 5 is attached thereto. Specifically, the portable recording medium 5 is attached to the external device 2b while the capsule endoscope 3 is moving inside the body cavities of the subject 1, and records data that is transmitted from the capsule endoscope 3. After the capsule endoscope 3 is discharged out of the subject 1, in other words, after the imaging inside the subject 1 is completed, the portable recording medium 5 is detached from the external device 2b and attached to the display device 4 so that the data recorded therein is read out by the display device 4. By applying the portable recording medium 5 such as a Compact Flash (Registered Trademark) memory and the like to deliver the data between the external device 2b and the display device 4, unlike the case in which the external device 2b and the display device 4 are linked by wired connection, the subject 1 can freely move even while the body-cavity imaging is performed.

Figure 2:
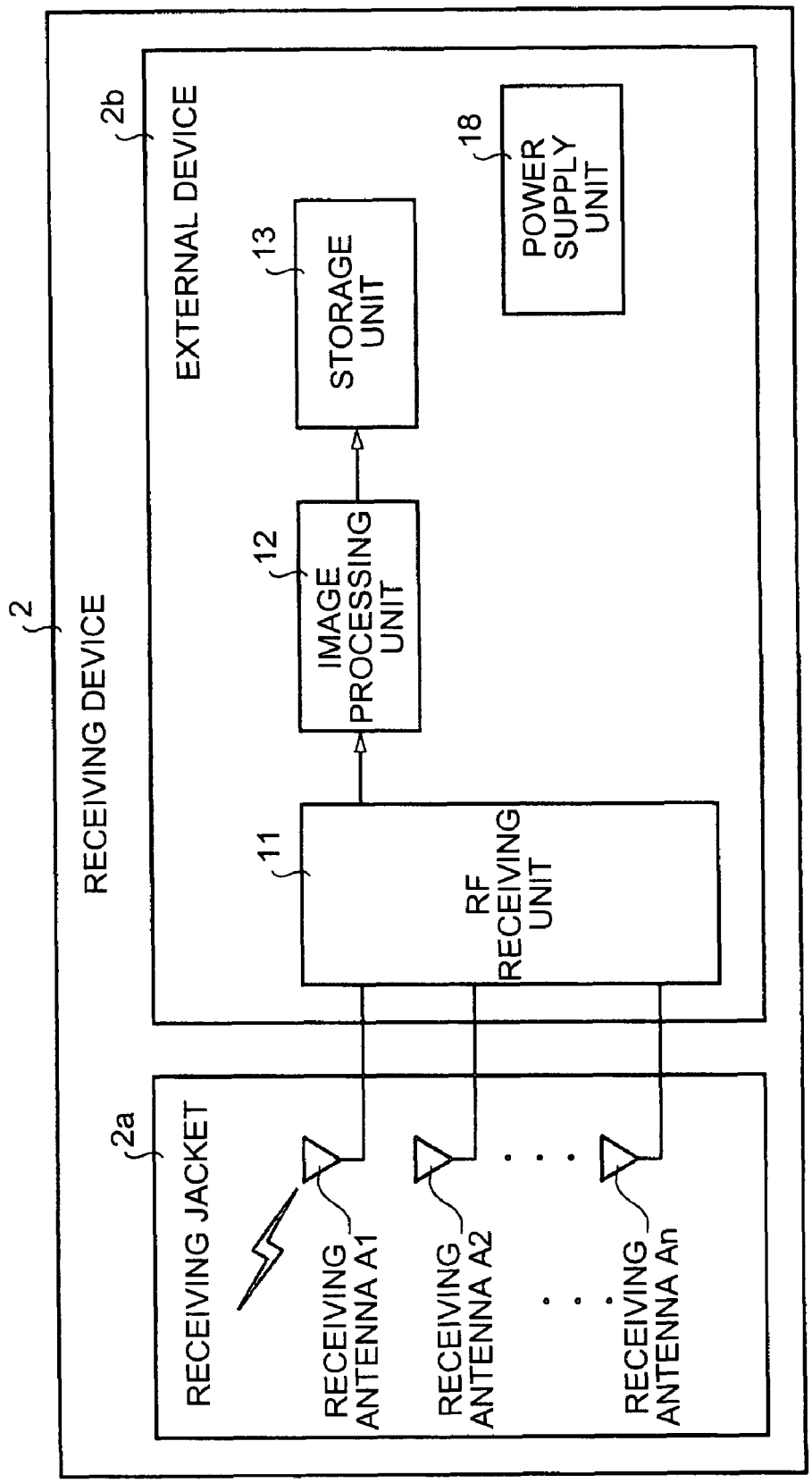
FIG. 2 is a block diagram schematically showing a configuration of a receiving device constituting the radio intra-subject information acquiring system shown in FIG. 1.

The receiving device 2 has a function as a receiving device that receives the body-cavity image data transmitted from the capsule endoscope 3. FIG. 2 is a block diagram schematically showing a configuration of the receiving device 2. As shown in FIG. 2, the receiving device 2 has a form wearable by the subject 1, and includes the receiving jacket 2a having receiving antennas A1 to An, and the external device 2b that performs, for example, processing of the radio signal received.

The external device 2b has a function of processing the radio signal that is transmitted from the capsule endoscope 3. Specifically, as shown in FIG. 2, the external device 2b includes an RF receiving unit 11 that performs predetermined processing on the radio signal received through the receiving antennas A1 to An, and that extracts, from the radio signal, the image data acquired by the capsule endoscope 3 to output the image data, an image processing unit 12 that performs necessary processing on the image data output, and a storage unit 13 that stores the image data that has been subjected to the image processing. Through the storage unit 13, the image data is recorded in the portable recording medium 5.

The external device 2b includes a power supply unit 18 provided with a predetermined capacitor, an AC power supply adaptor, or the like, and components of the external device 2b use the power supplied by the power supply unit 18 as a driving energy.

Figure 3:
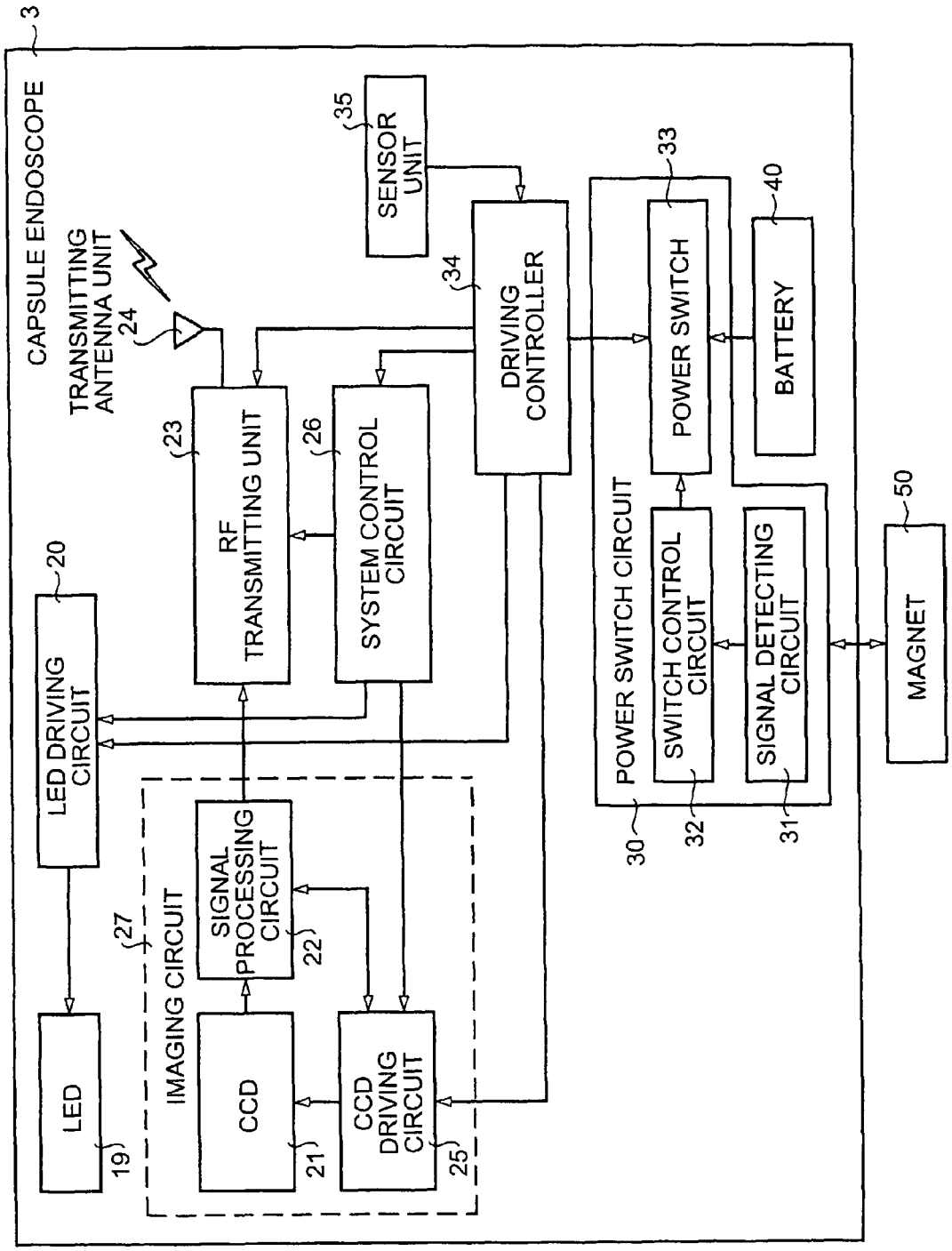
FIG. 3 is a block diagram showing a configuration of a capsule endoscope shown in FIG. 1.

The capsule endoscope 3 will be explained next. FIG. 3 is a block diagram schematically showing a configuration of the capsule endoscope 3. As shown in FIG. 3, the capsule endoscope 3 includes an LED 19 that lights an imaging area at the time of imaging of the inside of the subject 1, an LED driving circuit 20 that controls a driven state of the LED 19, a CCD 21 that serves as an imaging unit that performs imaging of the area lighted by the LED 19, and a signal processing circuit 22 that processes the image signal output by the CCD 21 into imaging information of a desirable format. Furthermore, the capsule endoscope 3 includes a CCD driving circuit 25 that controls a driven state of the CCD 21, an RF transmitting unit 23 that generates an RF signal by modulating the image data obtained through the imaging by the CCD 21 and processed by the signal processing circuit 22, a transmitting antenna unit 24 that transmits the RF signal output by the RF transmitting unit 23, and a system control circuit 26 that controls operations of the LED driving circuit 20, the CCD driving circuit 25, and the RF transmitting unit 23. The CCD 21, the signal processing circuit 22, and the CCD driving circuit 25 are collectively called an imaging circuit 27.

With these mechanisms provided, the capsule endoscope 3 acquires, by the CCD 21, image information of an examined area lighted by the LED 19 while the capsule endoscope 3 is inside the subject 1. The acquired image information is then subjected to signal processing by the signal processing circuit 22, converted into an RF signal by the RF transmitting unit 23, and then, transmitted to the outside through the transmitting antenna unit 24.

Furthermore, the capsule endoscope 3 includes a sensor unit 35 that detects a predetermined signal such as magnetic force, light, radio wave, and the like, and a driving controller 34 that controls, based on a value detected by the sensor unit 35, driving of the system control circuit 26 that collectively controls the LED driving circuit 20, the CCD driving circuit 25, the RF transmitting unit 23, and processing of each. The sensor unit 35 is implemented by, for example, a pH sensor, and detects whether the capsule endoscope 3 has reached a predetermined position inside the subject or not. Based on the result of detection by the sensor unit 35, the driving controller 34 controls the driving of each part. Thus, it is possible to suppress the power consumption.

Moreover, the driving controller 34 is supplied with electric power of a battery 40 serving as an energy supply source through a power switch 33 provided inside a power switch circuit 30. The battery 40 is implemented with, for example, a button battery of silver oxide or the like. The power switch 33 is in a sense a main power switch of the capsule endoscope 3. The power switch circuit 30 further includes a signal detecting circuit 31 and a switch control circuit 32. The signal detecting circuit 31 serving as an external-signal detecting unit that detects a signal from the outside of the capsule endoscope 3 is implemented with a lead switch, and is turned on and off in response to an approach and distancing of a magnet 50 to and from the lead switch. Specifically, the switch control circuit 32, which performs an on/off switching operation based on whether a magnetic force is applied to the lead switch or not, controls the power switch 33 to toggle the ON and OFF based on a control signal, that is, an on/off signal from the signal detecting circuit 31. The power switch 33 is turned ON and OFF in response to the magnet 50 before the capsule endoscope 3 is introduced into the subject, for an operation check and the like of the capsule endoscope 3.

Figure 4:
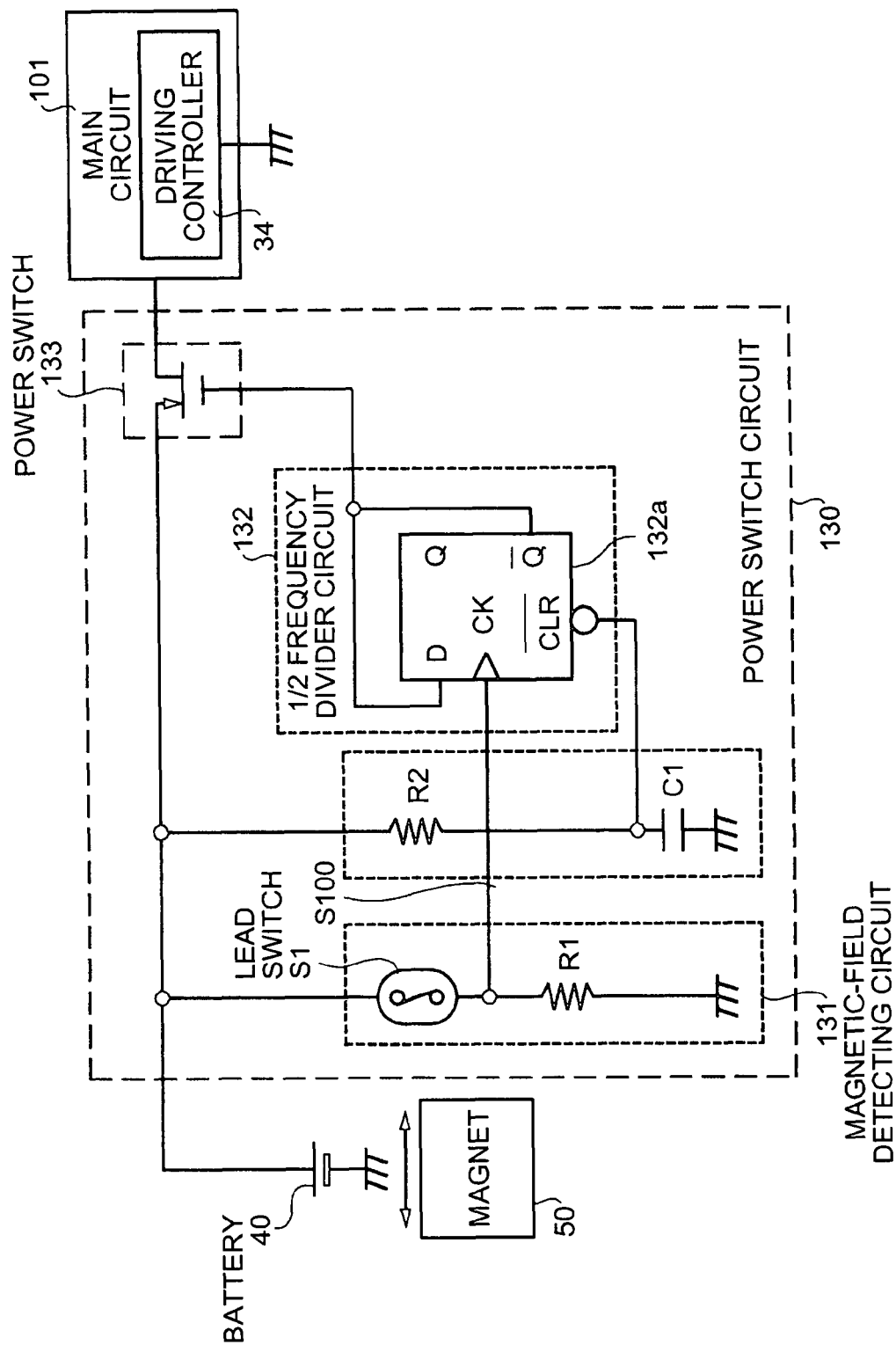
FIG. 4 is a circuit diagram showing a configuration of a power switch circuit shown in FIG. 3.

With reference to FIG. 4, a detailed configuration of the power switch circuit 30 will be explained. A power switch circuit 130 shown in FIG. 4 corresponds to the power switch circuit 30 shown in FIG. 3, a magnetic-field detecting circuit 131 corresponds to the signal detecting circuit 31, a ½ frequency divider circuit 132 corresponds to the switch control circuit 132, and a power switch 133 corresponds to the power switch 33. Further, a main circuit 101 means all circuits whose driving is controlled by the driving controller 34.

Figure 5:
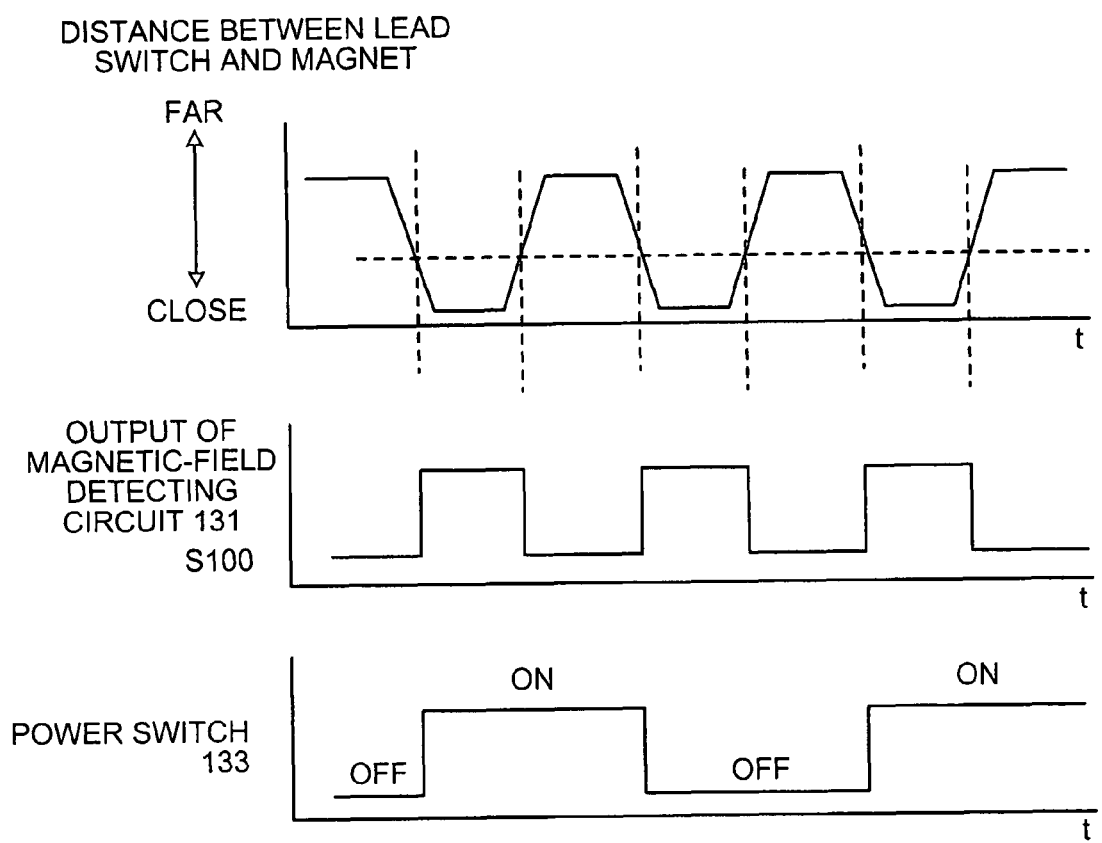
FIG. 5 is a timing chart showing an operation of the power switch circuit shown in FIG. 4.

The power switch circuit 130 includes the magnetic-field detecting circuit 131, the ½ frequency divider circuit 132, and the power switch 133. The magnetic-field detecting circuit 131 includes a lead switch S1 and a resistor R1 that are connected in series between a positive side of the battery 40 and a ground. The resistor R1 is arranged on a side of the ground. The lead switch S1 is turned into an off state when the magnet 50 is separated away from the lead switch S1, and turned into an on state when the magnet 50 is brought close to the lead switch S1, as shown in FIG. 5. An on/off signal is output to the ½ frequency divider circuit 132 from a connecting point of the lead switch S1 and the resistor R1 as a control signal S100.

The ½ frequency divider circuit 132 includes a D-type flip flop circuit 132a, and provides a signal obtained by frequency-dividing the control signal S100 by two as a final control signal to the power switch 133, as shown in FIG. 5. As a result, a set of operations of bringing the magnet 50 close to the magnetic-field detecting circuit 131 and distancing the magnet 50 away from the magnetic-field detecting circuit 131 induces a toggle operation of the power switch 133, i.e., switches the power switch 133 between the off state and the on state. Particularly, according to a set of operations of bringing the magnet 50 closer and distancing the magnet 50 away, the power switch 133 is turned from the off state to the on state, or from the on state to the off state, while maintaining either of the on state and the off state while the switching operation is not performed. In other words, even if the magnet 50 does not apply magnetic force to the lead switch S1 constantly, the power switch 133 can maintain a certain state, thus a function as a state maintaining unit is achieved. The D-type flip flop circuit 132a can be a T-type flip flop circuit or other types of circuits as long as ½ frequency division is achieved. Moreover, to a clear terminal CLR in the D-type flip flop circuit 132a, a resistor R2 is connected on the positive side of the battery 40, and a capacitor C1 on a side of a ground, so that the on/off state of the power switch 133 after the battery 40 is mounted is determined. The resistor R2 and the capacitor C1 can be omitted if the on/off state of the power switch 133 after the battery 40 is mounted can be either of the states.

Second Embodiment

A second embodiment of the present invention will be explained next. In the second embodiment, a power switch is turned on and off by the on/off operation same as that of the lead switch, and a direct current flowing through a power switch circuit when the power switch is in the off state is eliminated to lower the power consumption.

Figure 6:
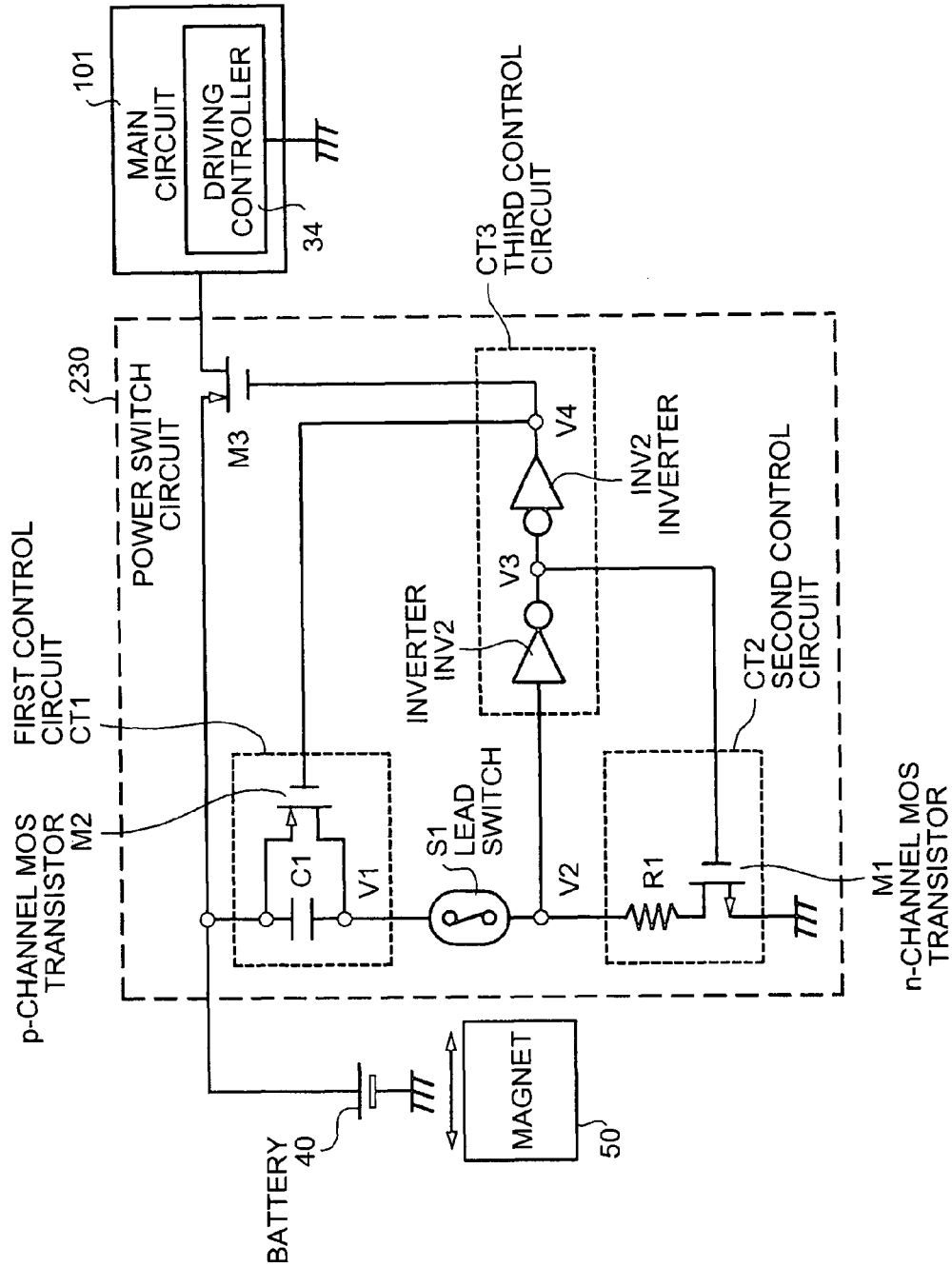
FIG. 6 is a block diagram showing a configuration of a power saving circuit in a power switch circuit of a capsule endoscope according to a second embodiment of the present invention.

FIG. 6 is a circuit diagram showing a configuration of a power saving circuit in a power switch circuit of a body-insertable apparatus (capsule endoscope 3) according to the second embodiment of the present invention. As shown in FIG. 6, a power switch circuit 230 includes the lead switch S1 and a power switch M3. A first control circuit CT1 is arranged between the positive side of the battery 40 and the lead switch S1, and a second control circuit CT2 is arranged between the lead switch S1 and the ground. Furthermore, a third control circuit CT3 is arranged between a connecting point of the lead switch S1 and the second control circuit CT2 and a gate of the power switch M3.

In the third control circuit CT3, inverters INV1 and INV2 are connected in series. In the second control circuit, the resistor R1 and an n-channel MOS transistor M1 are connected in series. The n-channel MOS transistor M1 is connected to the ground, and a gate thereof is connected to an output terminal of the inverter INV1. On the other hand, in the first control circuit CT1, a capacitor C1 and a p-channel MOS transistor M2 are connected in parallel, and a gate thereof is connected to an output terminal of the inverter INV2. Therefore, both the p-channel MOS transistor M2 and the n-channel MOS transistor M1 are in the off state when the power switch M3 is off, thereby suppressing direct-current power consumption when the power switch M3 is off.

Figure 7:
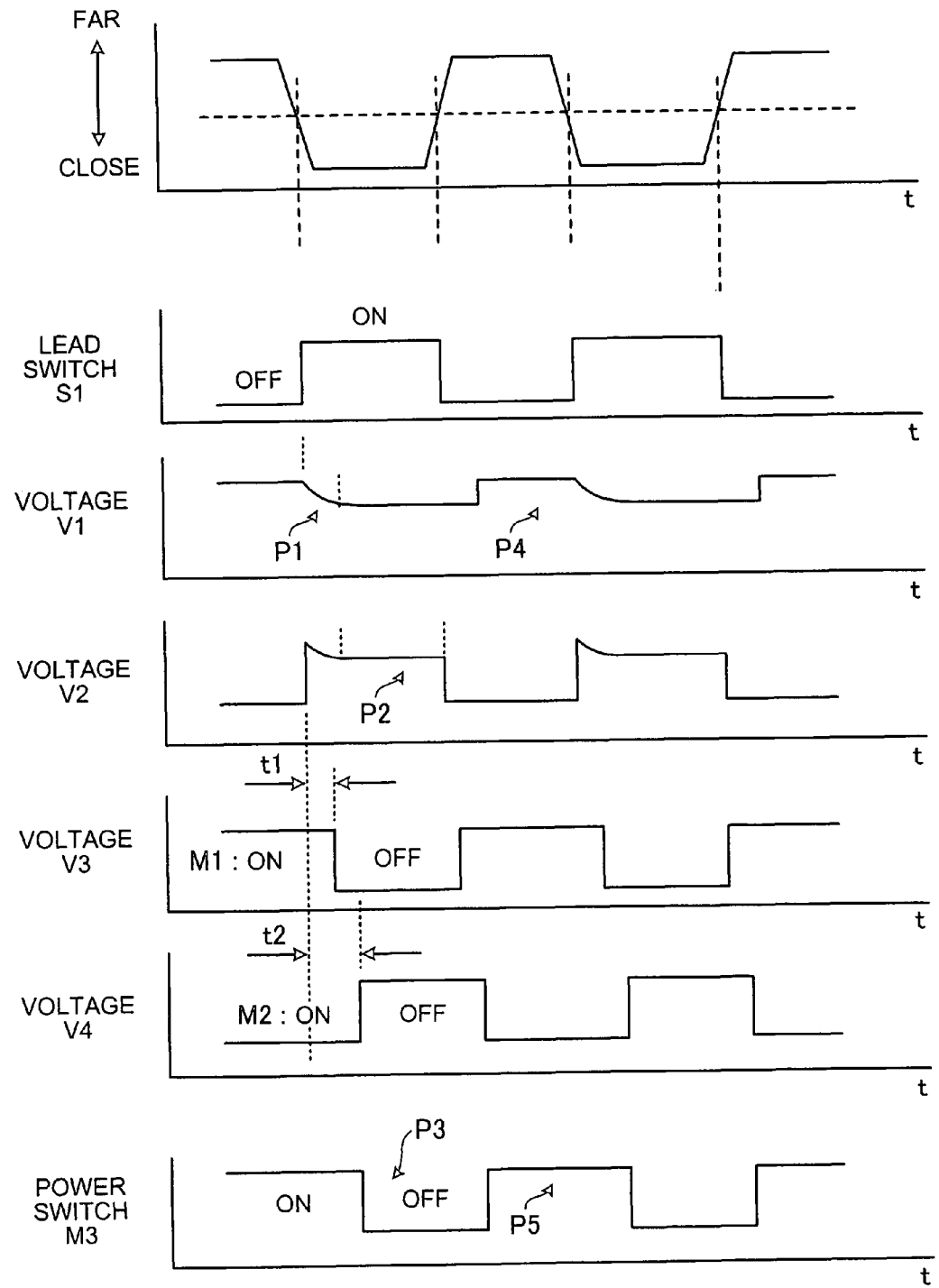
FIG. 7 is a timing chart showing an operation of the power switch circuit shown in FIG. 6.

With reference to a timing chart shown in FIG. 7, an operation of the power switch circuit 230 will be explained. First, when the magnet 50 is separated away from the lead switch S1, the lead switch S1 is turned into the off state, and when the magnet 50 is brought close to the lead switch S1, the lead switch S1 is turned into the on state. When the lead switch S1 is turned from the off state into the on state, a voltage V1 of the capacitor C1 on a side of the lead switch starts decreasing at a time constant of the capacitor C1 and the resistor R1. On the other hand, a voltage V2 of the resistor R1 on a side of the lead switch S1 once increases from a low level to be the same level as the voltage V1, which is a high level, because the lead switch S1 is turned into the on state, and then, starts decreasing at the time constant of the capacitor C1 and the resistor R1 in a similar manner as the voltage V1.

Thereafter, the n-channel MOS transistor M1 is turned off when a delay time t1 is elapsed from a time point when the lead switch S1 is turned on. By turning off the n-channel MOS transistor M1, decrease of the voltages V1 and V2 is suppressed. After a delay time t2 is elapsed, the p-channel MOS transistor M2 is turned off, and thus, the capacitor C1 is electrically charged, thereby maintaining the off state. In addition, the power switch M3 is turned off at the same time.

On the other hand, when the lead switch S1 is turned into the off state from the on state, a positive feedback loop is formed with the inverter INV1, the n-channel MOS transistor M1, and the resistor R1, and the voltage V2 attains a low level and a voltage V3 at an output end of the inverter INV1 attains a high level. Further, a voltage V4 at an output end of the inverter INV2 attains a low level, and as a result, the p-channel MOS transistor M2 is turned on, the capacitor C1 discharges the electrical charges, the power switch M3 is turned on when the voltage V1 attains the high level, and power is supplied to the main circuit 101.

With such a configuration, it is possible to eliminate current consumption during the power switch M3 is off, whereby a waste of the battery can be suppressed.

The overall configuration of the power switch circuit according to a modification of the second embodiment will be explained next.

Figure 8:
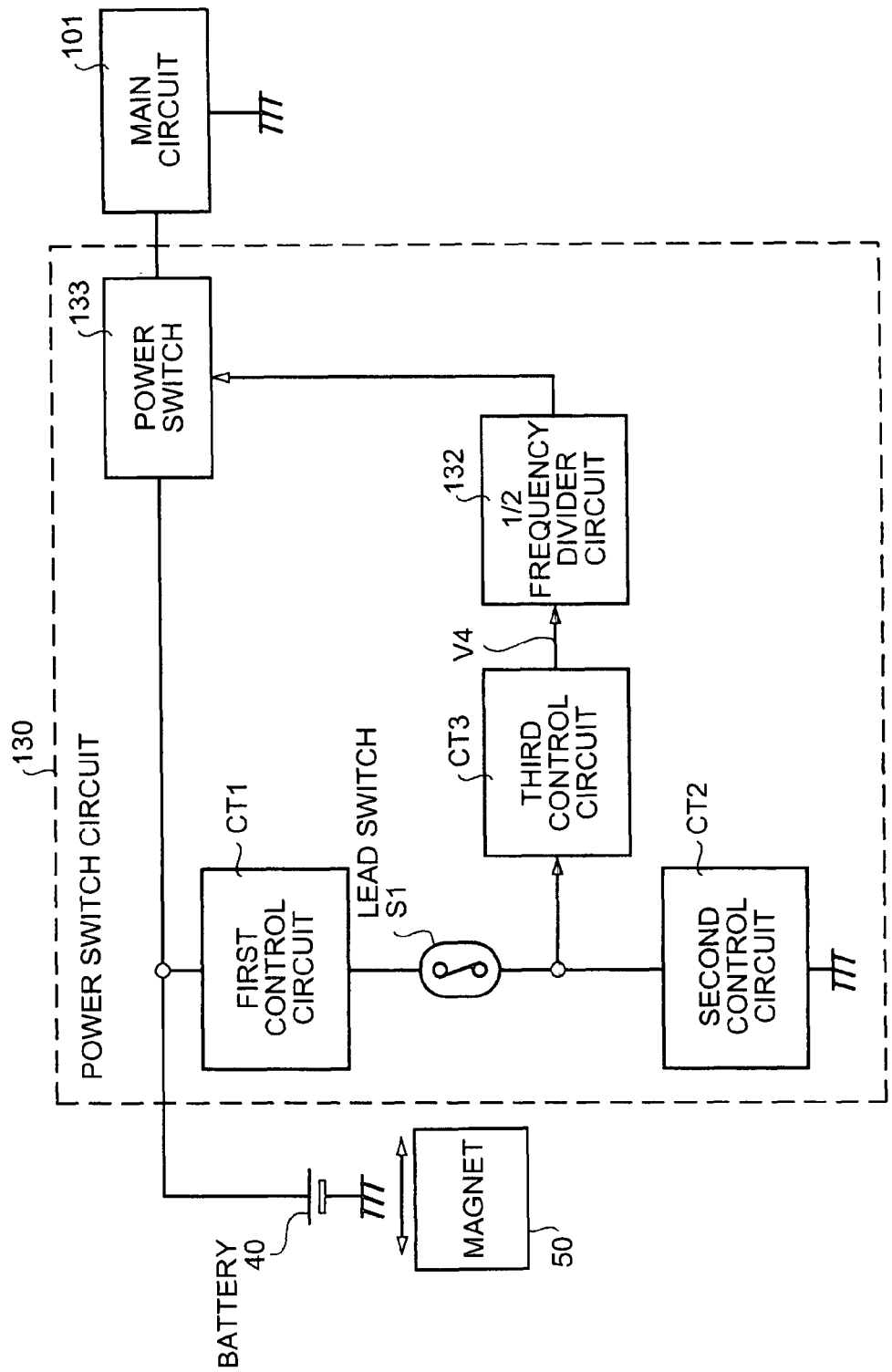
FIG. 8 is a block diagram showing an overall configuration of a power switch circuit of a capsule endoscope according to a modification of the second embodiment of the present invention.

FIG. 8 is a block diagram showing an overall configuration of the power switch circuit according to the modification of the second embodiment of the present invention. As shown in FIG. 8, a power switch circuit 330 is configured such that an output of the third control circuit CT3 shown in FIG. 4 is input to the ½ frequency divider circuit 132 that is the same as the ½ frequency divider circuit described in the first embodiment, and a control signal that is frequency-divided by two is output to the power switch 133.

Figure 9:
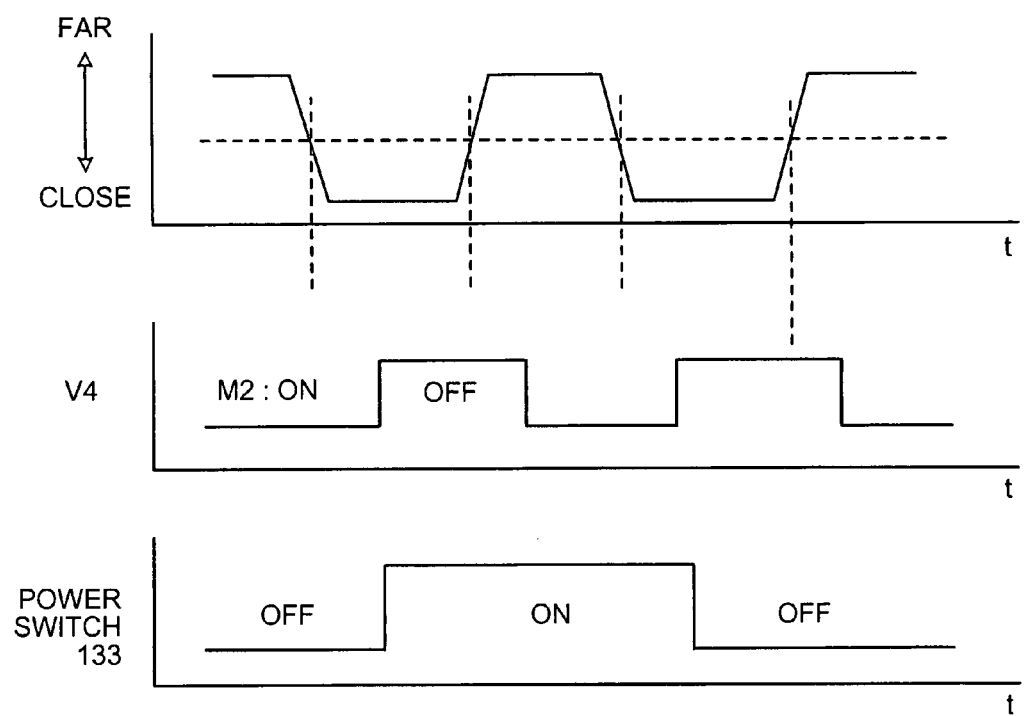
FIG. 9 is a timing chart showing an operation of the power switch circuit shown in FIG. 8.

According to the modification of the second embodiment, it is possible to eliminate current consumption during the power switch 133 is off so that waste of the battery 40 is suppressed, and because the power switch 133 is turned on and off by the control signal that is frequency-divided by two, as shown in FIG. 9, it is not necessary to maintain relation between the magnet 50 and the lead switch S1 in a close state or in a separated state, whereby a switching operation is simplified.

Third Embodiment

A third embodiment of the present invention will be explained next. In the third embodiment, the power switch 133 is made to be securely turned on and off even when the magnet 50 cannot be arranged near the lead switch S1.

Figure 10:
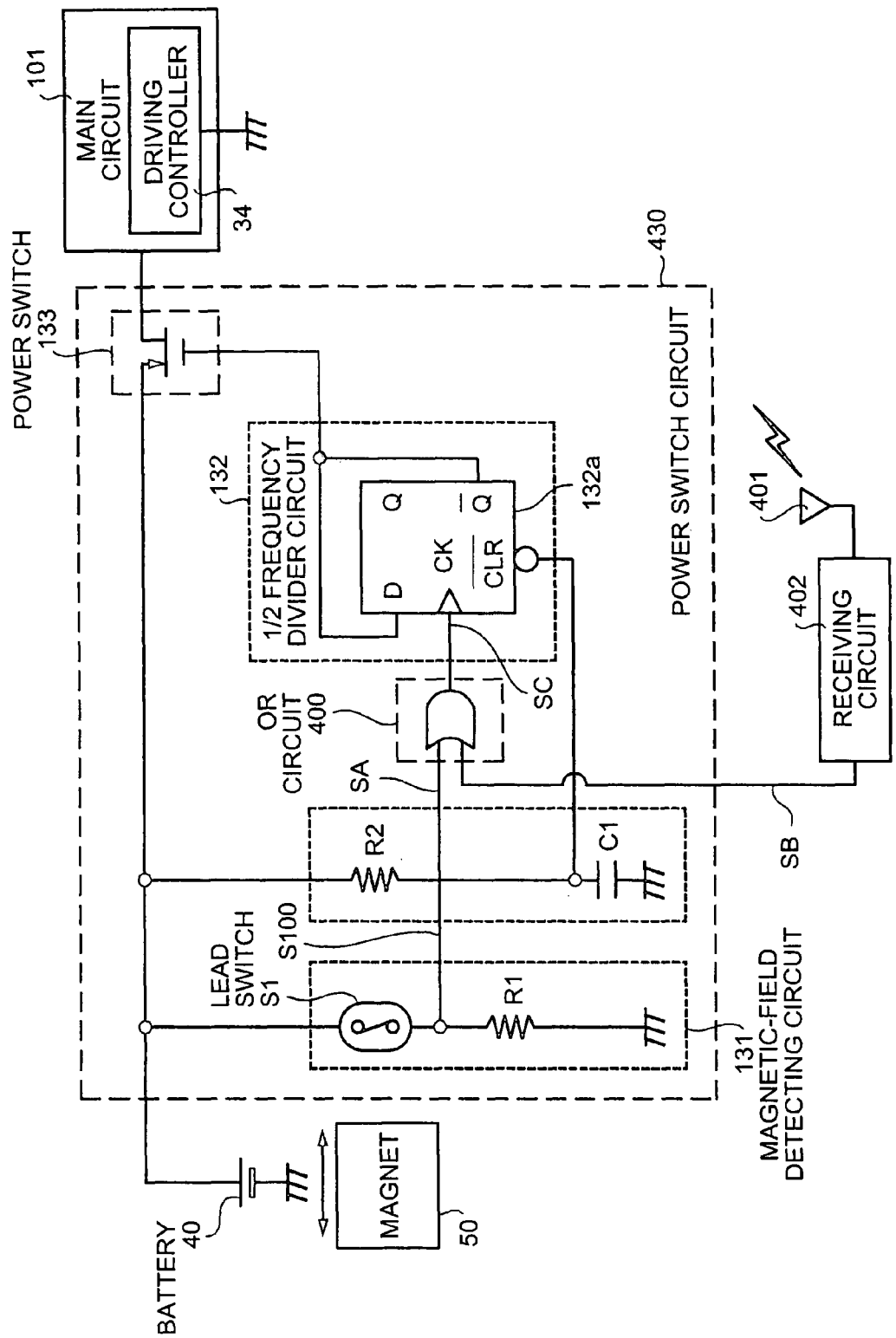
FIG. 10 is a block diagram showing a configuration of a power switch circuit of a capsule endoscope according to a third embodiment of the present invention.

FIG. 10 is a block diagram showing a configuration of a power switch circuit according to the third embodiment of the present invention. As shown in FIG. 10, a power switch circuit 430 includes an antenna 401, a receiving circuit 402, and an OR circuit 400 in addition to the configuration of the power switch circuit 130 described in the first embodiment. Other components are the same as those of the first embodiment and like reference letters or numerals refer to like constituent parts.

As shown in FIG. 10, the receiving circuit 402 receives a specific radio frequency signal, and inputs a control signal SB into the OR circuit 400 when this radio frequency signal is received. On the other hand, the magnetic-field detecting circuit 131 inputs a control signal SA into the OR circuit 400. The OR circuit 400 calculates a logical sum of the control signals SA and SB input, and inputs a result of the calculation to the ½ frequency divider circuit 132 as a control signal SC. The power switch 133 is controlled by output from the ½ frequency divider circuit 132.

Figure 11:
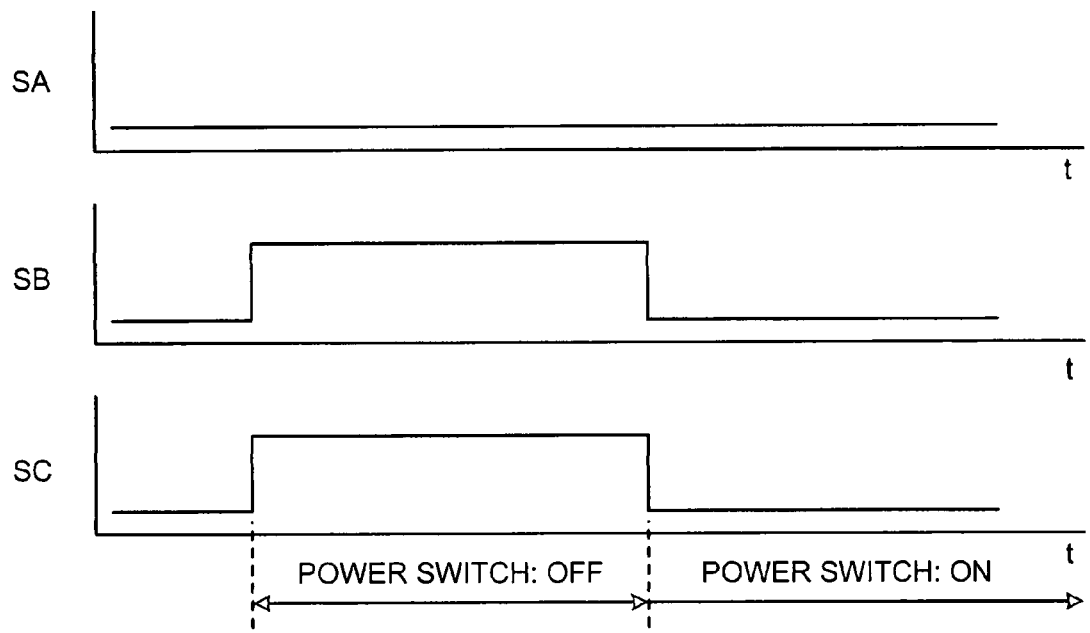
FIG. 11 is a timing chart showing an operation of the power switch circuit shown in FIG. 10.

For example, when the magnet 50 cannot be brought close to the lead switch S1, and a specific radio frequency signal is transmitted from a radio device not shown, as shown in FIG. 11, the receiving circuit 402 receives the specific radio frequency signal through the antenna 401 and outputs, to the OR circuit 400, the control signal SB to turn on the power switch 133. The ½ frequency divider circuit 132 operates in response, and the control signal to turn on the power switch 133 is output.

Note that the receiving circuit 402 described in the third embodiment is one example, and various detecting circuits that detect control signals transmitted by wireless communication from, for example, an infrared receiver, an optical receiver, or the like can be applied. The detecting circuit is also not limited to different types or same types of detecting circuits. Further, such a configuration can be applied that outputs from three or more detecting circuits are input to the OR circuit 400 to calculate logical sum thereof, and the power switch 133 is turned on by an instruction from any one of the detecting circuits to turn on the power switch 133.

Fourth Embodiment

A fourth embodiment of the present invention will be explained next. In the fourth embodiment, switching can be securely performed even when the lead switch S1 malfunctions because of noises or the like.

Figure 12:
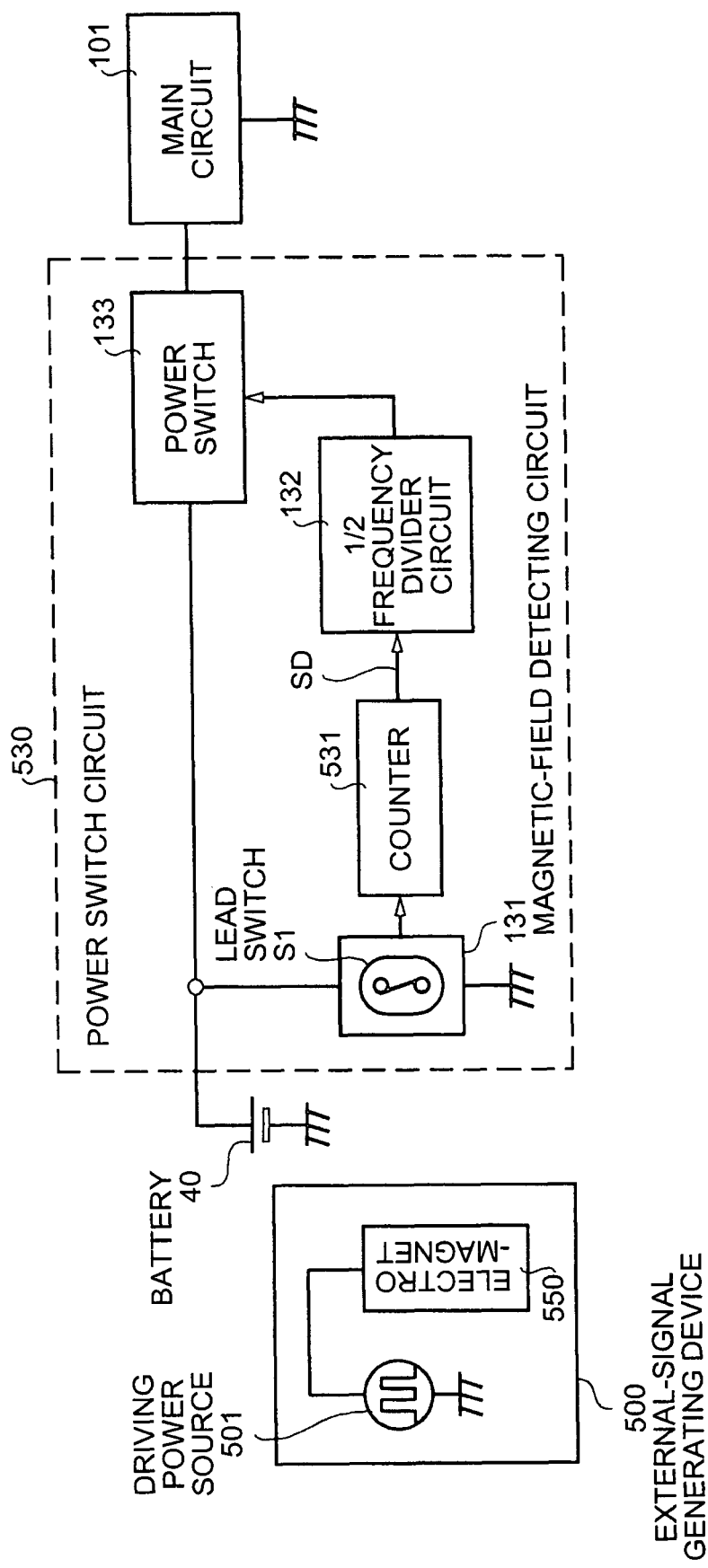
FIG. 12 is a block diagram showing a configuration of a power switch system in a capsule endoscope according to a fourth embodiment of the present invention.

FIG. 12 is a block diagram showing a configuration of a power switch system including a power switch circuit according to the fourth embodiment of the present invention. The power switch system is one example of the body-insertable apparatus system. As shown in FIG. 12, the power switch system mainly includes an external-signal generating device 500 and a power switch circuit 530. The external-signal generating device 500 includes a driving power source 501 that generates successive pulse, and an electromagnet 550. The electromagnet 550 generates a magnetic field pulse corresponding to the successive pulse generated by the driving power source 501.

On the other hand, the power switch circuit 530 includes a counter 531 that counts pulse control signals corresponding to the magnetic field pulse from the magnetic-field detecting circuit 131, and that outputs, when equal to or more than a predetermined number of the successive pulse control signals are obtained, one of the control signals to the ½ frequency divider circuit 132. Other configurations are the same as those of the first embodiment, and like reference letters or numerals refer to like constituent parts.

Figure 13:
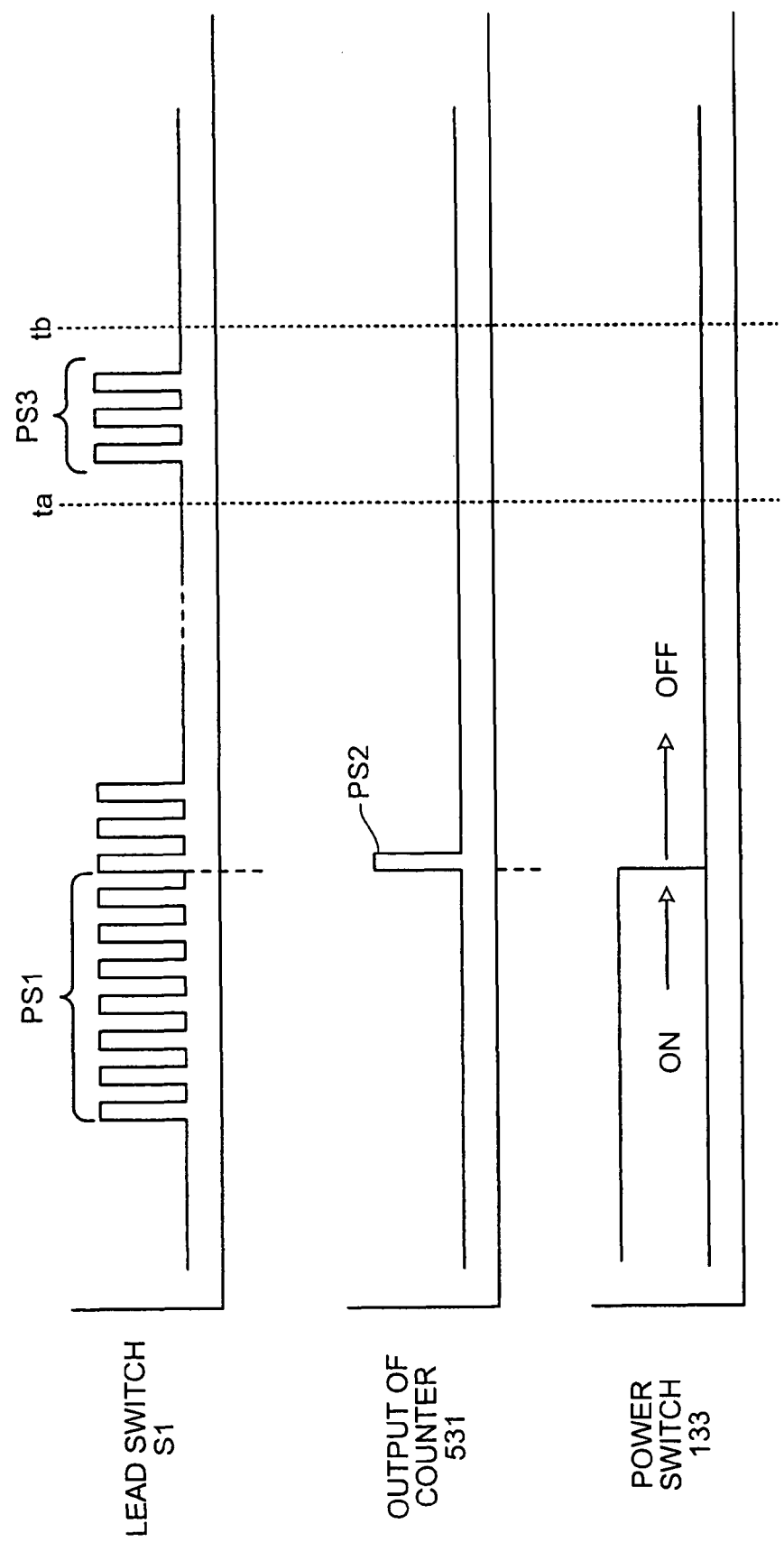
FIG. 13 is a timing chart showing an operation of the power switch system shown in FIG. 12.

The counter 531, for example as shown in FIG. 13, when receiving seven successive pulses as a control signals corresponding to the magnetic pulse from the lead switch S1, determines that each pulse is not attributable to noises or malfunctions, and outputs a pulse PS2 as the control signal to the power switch 133 through the ½ frequency divider circuit 132. FIG. 13 shows that the power switch 133 is switched from the on state to the off state in response to the pulse PS2. On the other hand, since the number of successive pulses of a pulse PS3 in a period between ta and tb is three, the pulses of the pulse PS3 are determined to be generated due to malfunctions or the like, and the switching control is not executed.

Figure 14:
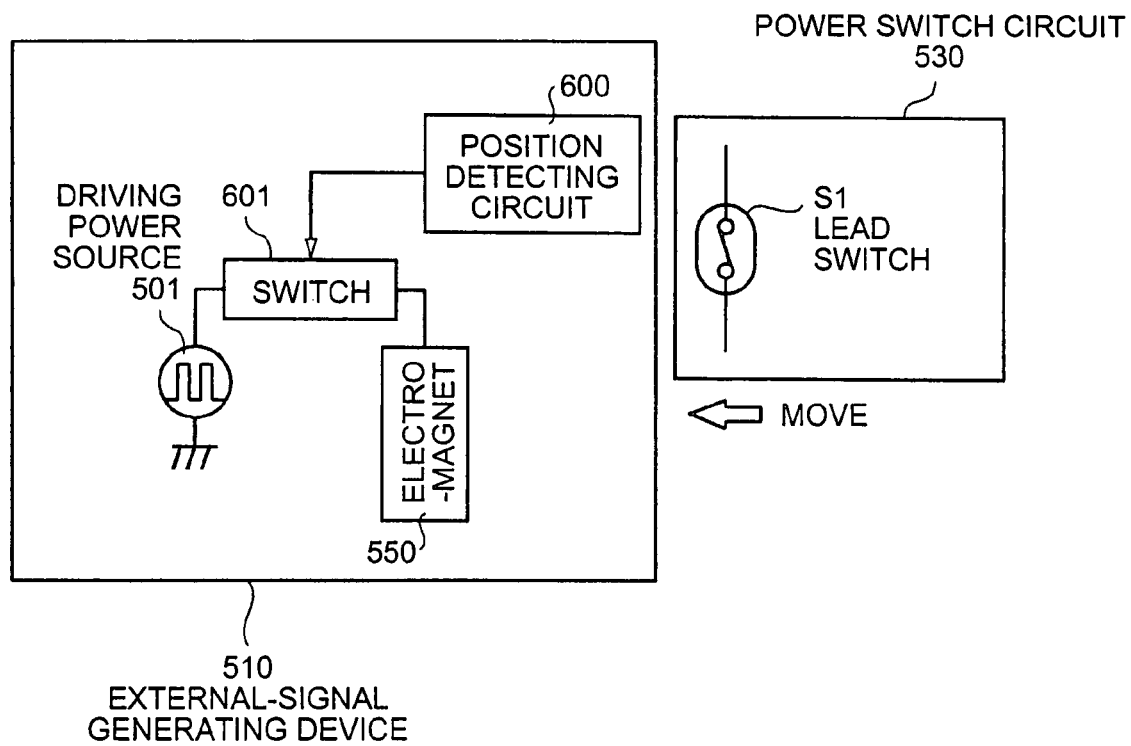
FIG. 14 is a block diagram showing a configuration of a power switch system in a capsule endoscope according to a modification of the fourth embodiment of the present invention.

FIG. 14 is a block diagram showing a schematic configuration of a power switch system according to a modification of the fourth embodiment of the present invention. In the power switch system shown in FIG. 14, a position detecting circuit 600 and a switch 601 are further provided in the external-signal generating device 510. The switch 601 is arranged between the driving power source 501 and the electromagnet 550, and is switched by a position detecting signal from the position detecting circuit 600.

The position detecting circuit is implemented with, for example, an imaging unit such as a camera, and when the power switch circuit 530 and the like as a predetermined imaging object is closely imaged, generates the position detecting signal to turn on the switch 601. Thus, the electromagnet 550 generates a magnetic pulse corresponding to the driving pulse of the driving power source 501. Therefore, the magnetic pulse is generated by the electromagnet 550 when the position detecting circuit 600 is positioned close to the power switch circuit 530, and the magnetic pulse is not generated by the electromagnet 550 when the position detecting circuit 600 is positioned far away from the power switch circuit 530. Thus, it is possible to suppress the power consumption of the driving power source.

Fifth Embodiment

A fifth embodiment of the present invention will be explained next. In the fifth embodiment, the initial setting of a capsule endoscope 103 can be performed with low power consumption.

Figure 15:
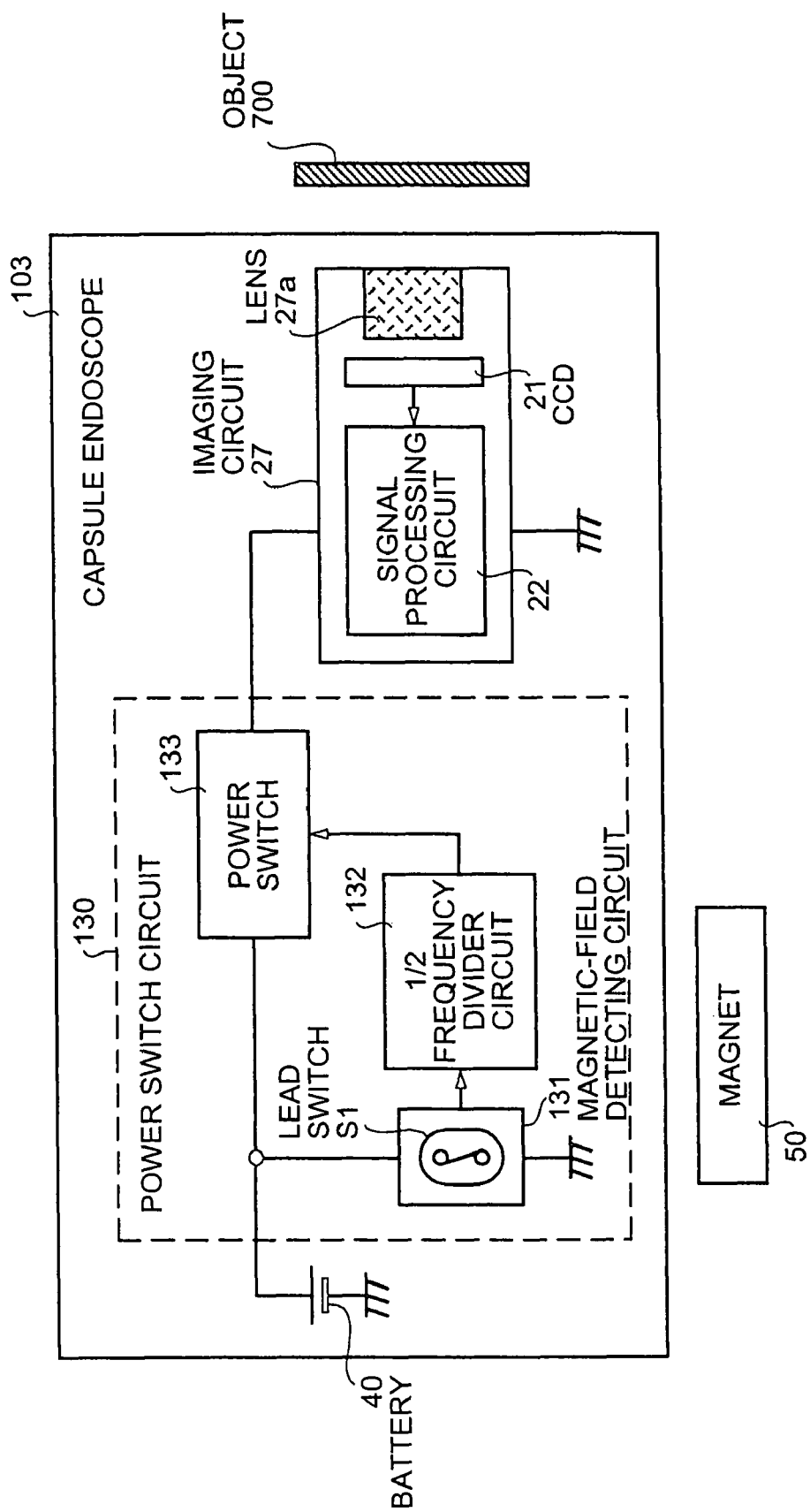
FIG. 15 is a block diagram showing a configuration of a capsule endoscope according to a fifth embodiment of the present invention.

FIG. 15 is a block diagram showing a configuration of the capsule endoscope 103 according to the fifth embodiment of the present invention. As shown in FIG. 15, the capsule endoscope 103 includes the imaging circuit 27 that is connected to the power switch circuit 130, and an object 700 used for the initial setting, such as white balance, sensitivity setting, and shading correction, is provided in advance, within the field of view of imaging by the imaging circuit 27. The sensitivity setting includes settings of exposure, amplifier gain, an amount of light for the lighting, etc.

With reference to a flowchart shown in FIG. 16, procedures of an initial setting process will be explained. The initial setting process is performed by the system control circuit 26 according to a program set in advance. First, the power switch 133 is turned off by the magnet 50 (step S101). The magnet 50 is then brought close to the capsule endoscope 3 (step S102) to set the power switch 133 in the on state (step S103).

Since the object 700 serving as a chart is arranged in advance in an imaging area, the imaging circuit 27 starts the initial setting immediately after the power is on (step S104). The procedure is then transited to a normal imaging or to other inspection processing (step S105), and the main process is finished.

In the fifth embodiment, since the object such as a chart image is arranged in advance within the field of view of imaging and the initial setting is performed upon the power-on, a swift initial setting can be realized with an efficient power consumption without unnecessarily power consumption.

In the first to the fifth embodiments described above, a combination of the magnet 50 and the lead switch S1 has been explained. Not limited thereto, the present invention is similarly applicable to apparatus or system in which other detecting circuits, such as optical detector including infrared detector and an electromagnetic wave detector, are used to detect control signals wirelessly transmitted.

INDUSTRIAL APPLICABILITY

As described above, the present invention relates to a body-insertable apparatus that is used in a state of being introduced inside a body of a subject and that performs a predetermined function inside the subject, and a body-insertable apparatus system, and is particularly useful for a capsule endoscope.

The invention claimed is:
1. A body-insertable apparatus that performs a predetermined function inside the body of the subject, comprising:
a function executing unit that performs the predetermined function;
an energy supply source that supplies with energy to be used to drive the function executing unit;
an external-signal detecting unit that detects an external control signal input from outside the body-insertable apparatus, and that generates a control signal based on a detection state of the external control signal;
a switch that controls supply of the energy to the function executing unit from the energy supply source; and
an energy supply control unit that causes the switch to toggle in accordance with the control signal from the external-signal detecting unit, wherein the energy supply control unit includes a state maintaining unit that maintains the detection state of the external control signal detected by the external-signal detecting unit, and the state maintaining unit includes:
an output control circuit that generates a reverse signal obtained by reversing the control signal output from between the external-signal detecting unit and a ground, and that outputs a re-reverse signal obtained by further reversing the reverse signal to the switch;
a first control circuit including a capacitor that is arranged between the energy supply source and the external-signal detecting unit, and a first switch that is connected to the capacitor in parallel and that is turned off and on based on the re-reverse signal indicating on and off respectively; and
a second control circuit including a resistor that is arranged between an output end of the external-signal detecting unit and a ground, and a second switch connected in series on a side of the ground and that is turned on and off based on the reverse signal indicating on and off respectively.
2. The body-insertable apparatus according to claim 1, further comprising a ½ frequency divider circuit that frequency-divides the re-reverse signal output from the output control circuit by two, and that causes the switch to toggle according to the control signal that has been frequency-di- vided by two, the ½ frequency divider circuit arranged between the output control circuit and the switch.

3. The body-insertable apparatus according to claim 2, wherein at least one of the ½ frequency divider circuit and the output control circuit includes a CMOS circuit.

4. The body-insertable apparatus according to claim 1, further comprising:
   a different external-signal detecting unit that detects a different external signal of which a detection mode is different, and that transmits a control signal to cause the switch to toggle to the energy supply control unit according to a detection state; and
   a logical sum circuit that calculates a logical sum of the control signal output from the external-signal detecting unit and the control signal output from the different external signal detecting unit and outputs the logical sum to the switch.

5. The body-insertable apparatus according to claim 4, wherein the different external-signal detecting unit is a radio receiving unit that receives a radio signal.

6. The body-insertable apparatus according to claim 1, further comprising an imaging unit as the function executing unit, wherein
   an object for an initial setting is provided, externally to the body-insertable apparatus, in advance within an imaging area of the imaging unit, and
   the imaging unit includes a control unit that performs the initial setting at a time of initial energy supply.

7. The body-insertable apparatus according to claim 1, wherein at least one of the switch, the first switch, and the second switch includes a MOS transistor.

8. The body-insertable apparatus according to claim 1 wherein the external-signal detecting unit is a lead switch that detects a magnetic force as the external control signal.

9. The body-insertable apparatus system according to claim 1 wherein the external control signal is a magnetic field.

10. The body-insertable apparatus system according to claim 1 wherein the external control signal is an infrared.

11. The body-insertable apparatus system according to claim 1 further comprising:
    a sensor unit that detects one of magnetic force, light, radio wave, or pH; and
    a driving controller that controls driving of the function executing unit and the switch based on a result of detection by the sensor unit.

12. A body-insertable apparatus system comprising:
    an external-signal generating device that generates a successive pulse signal as an external control signal; and
    a body-insertable apparatus that includes
       a function executing unit that performs a predetermined function inside a body of a subject;
       an energy supply source that supplies with energy to be used to drive the function executing unit;
       an external-signal detecting unit that detects the external control signal input from outside;
       a measuring unit that measures a number of pulses in the successive pulse signal based on a result of detection by the external-signal detecting unit, and that outputs a control signal on detecting a predetermined number of pulses successively and refrains from outputting a control signal by determining that pulses are a noise when a number of the pulses detected successively is smaller than the predetermined number;
       a switch that controls supply of the energy to the function executing unit from the energy supply source; and
       an energy supply control unit that causes the switch to toggle according to the control signal from the measuring unit.

13. The body-insertable apparatus system according to claim 12, wherein the external-signal generating device further includes a position detecting unit that detects approach of the body-insertable apparatus, and
    the external-signal generating device generates the successive pulse signal when the approach of the body-insertable apparatus is detected.

* * * * *